United States Patent [19]

Tabb et al.

[11] 4,440,724
[45] Apr. 3, 1984

[54] COMPOSITION FOR DETECTING KETONE BODIES AND METHOD OF PREPARATION

[75] Inventors: David L. Tabb, Beaumont; Janine P. Burrows, Orange, both of Tex.

[73] Assignee: Helena Laboratories Corporation, Beaumont, Tex.

[21] Appl. No.: 438,063

[22] Filed: Nov. 1, 1982

[51] Int. Cl.$^3$ ............................................. G01N 33/64
[52] U.S. Cl. ......................................... 422/56; 427/2; 436/128
[58] Field of Search .................... 422/56, 57; 436/128, 436/130; 427/2

[56] References Cited

U.S. PATENT DOCUMENTS

| 3,880,590 | 4/1975 | Ogawa et al. ......................... 422/56 |
| 4,147,514 | 4/1979 | Magers et al. .................... 422/56 X |
| 4,184,850 | 1/1980 | Wabenstein ....................... 422/56 X |

FOREIGN PATENT DOCUMENTS 1153920  9/1963  Fed. Rep. of Germany ...... 436/128

*Primary Examiner*—Arnold Turk

*Attorney, Agent, or Firm*—Cullen, Sloman, Cantor, Grauer, Scott & Rutherford

[57] ABSTRACT

A composition, test means, method of making test means and process for the detection of ketone bodies in human fluids. The composition includes a chromogen and, discrete therefrom, a combination of a metal salt, a primary amine and a chelator for the metal. The composition may be in tablet form or in separately sequentially impregnated layers on a carrier. If the composition is in tablet form, the composition is a dry combination of the chromogen, the metal salt, primary amine acid and the chelator. If the test means is formed on a carrier as separately impregnated layers, the chromogen is impregnated onto the carrier, the impregnated carrier is then dried, and then the combination of the primary amine, metal salt and chelator in liquid form are impregnated over the dry chromogen and thereafter the impregnated carrier is dried. The chelator adds to the buffer capacity of the inventive composition, and the present composition, whether in tablet form or impregnated on a carrier has a high buffer capacity and is accurate over a wide range of acidity and alkalinity.

6 Claims, No Drawings

COMPOSITION FOR DETECTING KETONE BODIES AND METHOD OF PREPARATION

BACKGROUND OF THE INVENTION

This invention relates generally to a composition and method for detecting ketone bodies in human fluid and, more particularly, to an improved composition, test means, method of making a test means and process for the detection of ketone bodies in human fluids which is accurate over a wide range of acidity and alkalinity.

It is known that ketosis takes place owing to insufficient intake to sugars or other disorders of sugar availability in living bodies. In patients with ketosis, ketone bodies such as acetoacetic acid, acetone or beta hydroxybutyric acid (considered to be a ketone body) increase in the blood and they are excreted primarily as acetoacetic acid in the urine. Such ketosis indicates probable presence of one or more diseases such as diabetes, disorders of the digestive organs, renal insufficiency, uremia, malignant carcinoma, etc. Thus, detection of ketone bodies in body fluids such as urine, serum or plasma is important to provide early diagnosis of such diseases.

The use of chromogens such as soluble nitroprussides in the detection of ketone bodies has long been recognized. For example, as early as 1940, U.S. Pat. No. 2,186,902, to Fortune, disclosed a formulation where nitroprusside is reacted in the presence of ammonia to develop particular colorations. In 1950, U.S. Pat. No. 2,509,140 to Free disclosed formulations for the detection of ketone bodies in urine where the formula contained the combination of water soluble nitroprusside, an aliphatic amino acid (glycine) and an alkaline material. Shortly thereafter, in 1951, U.S. Pat. No. 2,577,978 to Nicholls disclosed the addition of lactose or similar sugars to the formulation described in the Free patent to enhance the utility of the test and the reliability of results.

In 1961, U.S. Pat. No. 2,990,253 to Smeby described a test composition incorporated into a bibulous strip or stick. Since it is known that nitroprusside is unstable in an alkaline aqueous medium, the nitroprusside was kept separate using a two-step preparation method where the nitroprusside was first applied to the bibulous carrier in an acid aqueous medium, thus preserving the stability of the nitroprusside and, after the nitroprusside was dried, the carrier was dipped into a non-aqueous solution of organic bases such as amines or amino alcohols to achieve the necessary alkalinity for the bibulous strip. Such alkalinity was necessary because the nitroprusside per se functioned properly only at alkaline pH even though unstable at alkaline pH. The reference to the nitroprusside being unstable in an alkaline aqueous medium means that in such a solution the nitroprusside will react with certain negative ions including not only acetoacetate ions but even with hydroxy ions thus providing an unacceptable result by the formation of a yellow colored hydroxy ferricyanide. The reference to nitroprusside per se functioning properly only at alkaline pH means that as of the 1961 state of the art, the ketone ionized as a negative ion, to thus react with the nitroprusside, only in alkaline solutions.

There were, however, problems with the technique described in the Smeby patent. For example, the amines and amino alcohols are hygroscopic and volatile. Because the amines and amino acids are hygroscopic, when they absorb moisture from the air, the moisture provided the hydroxy ion and since the strip was alkaline this resulted in the aforementioned instability of the nitroprusside, e.g., this permitted the formation of hydroxy ferricyanide.

In 1965, U.S. Pat. No. 3,212,855 to Mast disclosed an improvement in the two-dip method of preparing a test strip or bibulous strip where the strip was first impregnated with an alkaline buffer and an amino acid combination. After drying, the strip was then impregnated with the combination of an alkali metal nitroprusside, an organic film-forming compound of acid pH and an organic solvent. The test strip prepared according to the description in the Mast patent resulted, however, in two problems. First, the organic solvent, dimethyl sulfoxide, is a health hazard and, second, the test strip had insufficient humidity stability to function properly. Thus, upon absorption of moisture, the nitroprusside hydrated, became alkaline and unstable.

Then, in 1975, U.S. Pat. No. 3,880,590 to Ogawa described a test strip made from a single dip or impregnation of a bibulous carrier into the combination of nitroprusside and a heavy metal salt such as nickel chloride. Again, a hazardous solvent, dimethyl sulfoxide, was used. The heavy metal salt provided a positive metal ion and shifted the ionization constant of the ketone so that the ketone ion was negatively charged in an acid pH solution. Hence the nitroprusside would theoretically function properly in an acid pH. If the body fluid such as urine was expected to be acidic, a buffer such as TRIS was added to the solution prior to dipping the bibulous carrier into the solution. There were, however, several problems and disadvantages with the system described in the Ogawa patent. The solution itself was unstable, there was low sensitivity to the ketone bodies and there was relatively no humidity stability. Lack of humidity stability is a serious shortcoming because of the hygroscopic nature of both the TRIS and the nitroprusside.

More recently, U.S. Pat. No. 4,147,514 issued to Magers and Tabb in 1979 disclosed an improved solution using nitroprusside in combination with at least one inorganic metal salt with the metal selected from the group of magnesium and calcium and, optionally, at least one primary amine. This is a one-dip application for impregnating the chemicals onto a bibulous carrier and exhibits humidity stability. However, the solution itself demonstrates some instability and a very low buffer capacity in that body fluids of a very high alkalinity or high acidity will give false readings.

Thus is may be seen, from a review of the above, that each of the prior art techniques yielded at least one significant drawback.

The present invention overcomes the shortcomings of the prior art by providing a new and improved test means, method of making the test means and method of testing for ketone bodies which is operable over a wide range of pH, where the solutions themselves are stable, where the test strip exhibits high humidity stability and where the system has a high degree of sensitivity to the ketones thus providing accurate, reliable results.

DESCRIPTION OF THE PREFERRED EMBODIMENT

The preferred embodiment of the present invention is a test strip of a bibulous matrix which is insoluble in and maintains its structural integrity when exposed to water or physiological fluids. The preferred method for the preparation of such a test strip is a two-dip application where a first solution is impregnated on the bibulous strip, dried, and then a second solution is impregnated on the bibulous strip and then dried. The term bibulous matrix or carrier includes paper, cellulose, wood, synthetic resin fleeces, glass fiber and woven and non-woven fabrics and the like. A preferred example, which has been used in the present invention is Schleicher and Scheull 2340A paper. Non-bibulous matrices or carriers which may be used include organo-plastic materials such as polystyrene, polypropylene or the like. Alternatively, the composition of the invention may be embodied in a carrier taking the form of a pressed or molded tablet containing conventional carrier or matrix material as is well known. The invention will first be described in the context of the impregnation of the bibulous carrier.

A first solution is prepared containing a chromogen and water. A second, separate solution includes a metal salt, a primary amine, a chelator and water.

The bibulous material is impregnated in the first solution and dried. The bibulous carrier is thereafter impregnated in the second solution and dried. The carrier thus twice impregnated may be immersed in body fluids and the chromogen exhibits a dark coloration such as purple in the presence of ketones.

The pH of the carrier after impregnation and drying is 7.0 or less and thus the chromogen is stable.

According to the principles of the present invention, the chromogen is a nitroprusside such as sodium nitroferricyanide or potassium nitroferricyanide. The first solution may contain, for example, 1.0 grams of sodium nitroferricyanide and 20.0 ml of water, i.e., about 5% nitroprusside.

The second solution contains a metal salt such as 3.0 grams of nickel chloride, a primary amine such as TAPS in the amount of 1.75–2.25 grams, and a chelator such as TRIS in the amount of 1.75–2.25 grams to which sufficient water is added to bring the volume of the solution to 40 ml.

TAPS is the primary amine N-Tris (hydroxymethyl) 3-aminopropane sulfonic acid. TRIS is tris-hydroxymethyl aminomethane. The TRIS functions not only as a metal chelator but also as a buffer.

The present invention has numerous advantages over the prior art. First, each solution is highly stable. It has been found that each solution once prepared, remains stable for at least one week. This stability of the solutions substantially reduces waste in that it is not necessary to use up all of the solution immediately in the impregnation of carriers.

A second advantage of the present invention is the very reactive nature thereof—even small quantities such as 5 milligrams per deciliter (100 ml) of acetoacetic acid in urine will be detected.

A third benefit of the present invention is humidity stability. Notwithstanding the hygroscopic nature of the chromogen, the chromogen remains slightly acidic until immersed in the body fluid. Thus, since chromogens such as nitroprussides are unstable as alkalines, it is desirable to maintain the chromogens slightly acidic.

A fourth and surprising benefit of the present invention is that even though TRIS is hygroscopic, the test strip impregnated with the combination of TRIS and TAPS is not hygroscopic.

A fifth benefit relates to the high buffer capacity of the present invention. For example, according to the prior art, if the body fluid had a high specific gravity the buffer capacity of the body fluid exceeded the buffer capacity of the test strips. Hence, the results according to the prior art were not reliable because the reaction with the chromogen was not carried out precisely within the pH range for which the solutions were designed.

We have discovered that the unique combination of both TRIS and TAPS greatly enhances the buffer capacity and thus accurate results may be obtained throughout a wide range of acidity and alkalinity of the sample or body fluid, and also if the body fluid has a high specific gravity. We believe that the reason for this unique result is that while TRIS is hygroscopic, the test strip is not hygroscopic when TRIS is used in combination with TAPS.

TEST RESULTS

To verify whether or not the present invention overcomes the shortcomings of the prior art by providing a stable, reliable test for ketones, five sample formulations were prepared. Each formulation included a first and second impregnations of the bibulous test strip as the following chart indicates. Specifically test strips were impregnated in the first solution, dried, impregnated in the appropriate second solution and dried. Sufficient test strips were impregnated so that each formulation could be evaluated for temperature stability, humidity stability and the ability to differentiate among various levels of ketones as will be described. The tests demonstrate the surprising and synergistic effect of combining both TAPS and TRIS in the formulation.

The following chart illustrates the formulations which were used.

CHART I

| | Sample Formulations | | | | |
|---|---|---|---|---|---|
| | I | II | III | IV | V |
| First Solution | | | | | |
| 5% sodium nitroferricyanide (aq) | 20 ml | 20 ml | 20 ml | 20 ml | 20 ml |
| Second Solution | | | | | |
| nickel chloride 6 H$_2$O | 3.0 g | 3.0 g | 3.0 g | 3.0 g | 3.0 g |
| TAPS | 2.0 g | 4.0 g | 0.0 g | 4.0 g | 0.0 g |
| TRIS | 2.0 g | 0.0 g | 4.0 g | 0.0 g | 4.0 g |
| H$_2$O | 40.0 ml | 40.0 ml | 40.0 ml | 40.0 ml | 40.0 ml |
| pH | 6.98 | 3.85 | 7.93 | Adjust to 6.95 | Adjust to 6.95 |

With respect to the above chart, it should be appreciated and understood that formulations II and IV are the same except that the pH of Formulation IV was adjusted by adding sodium hydroxide to achieve a pH of 6.95 (which was essentially the same pH as Formulation I). Similarly, Formulations III and V are the same except that the pH of Formulation V was adjusted downwardly to 6.95 by the addition of hydrochloric acid.

Test strips impregnated in each of the formulations were tested under various conditions; room temperature; 92% relative humidity for 15 hours; 92% relative humidity for 33 hours; an elevated temperature of 56° C. for 15 hours; and an elevated temperature of 56° C. for 48 hours. For each of the above conditions, each formulation was tested at concentrations of zero, 5, 15, 40, 80 and 160 milligrams per deciliter of acetoacetic acid in urine since it is important that the test strip be able to "differentiate", i.e., provide a quantitative indication of the amount of the acetoacetic acid (ketone) in the body fluid or sample being tested.

The following charts, one for each of the formulations, illustrates the result of the tests.

CHART II
RESULTS OF TEST WITH FORMULATION I

| Room Temp. | 92% Rel. Humidity | | 56° C. | |
|---|---|---|---|---|
| 15 hrs. and 33 hrs. differentiates | 15 hrs. differentiates | 33 hrs. slight discoloration but differentiates | 15 hrs. differentiates | 48 hrs. slight discoloration but differentiates |

Conclusion: Chart No. II demonstrates that Formulation I was temperature stable, humidity stable, and properly differentiated among the various levels or amounts of ketones.

CHART III
RESULTS OF TEST WITH FORMULATION II (NO TRIS)

| Room Temp. | | 92% Rel. Humidity | | 56° C. | |
|---|---|---|---|---|---|
| 15 hrs. differentiates | 33 hrs. will not differentiate | 15 hrs. differentiates | 33 hrs. will not differentiate | 15 hrs. and 48 hrs. no differentiation at lower ketone levels | |

Conclusion: Chart III demonstrates that Formulation II provides satisfactory results only if used promptly and at room temperature. Both the room temperature and the high humidity strips lost the ability to differentiate among various levels of ketones after 33 hours and the test strips subjected to elevated temperature lost the ability to differentiate among the lower levels of ketones.

CHART IV
RESULTS OF TEST WITH FORMULATION III (NO TAPS)

| Room Temp. | | 92% Rel. Humidity | | 56° C. | |
|---|---|---|---|---|---|
| 15 hrs. and 33 hrs. differentiates | 15 hrs. not differentiate | 33 hrs. lost reactivity | 15 hrs. differentiates | 48 hrs. not differentiates | |

Conclusion: Chart IV demonstrates that Formulation II provides satisfactory results only at room temperature, or at elevated temperature if used promptly. In the absence of TAPS, all of the test strips exhibited a green discoloration. Furthermore, the results of the humidity tests indicated that the absence of TAPS might have some bearing on humidity stability. But Formulation II (Chart III) which substituted TAPS for TRIS did not exhibit long term humidity stability. Surprisingly, however, the presence of both TAPS and TRIS (Chart II) was humidity stable. Similarly, while TAPS alone was not temperature stable and while TRIS alone was not temperature stable (long term), the combination of TRIS and TAPS exhibited both short term and long term temperature stability.

CHART V
RESULTS OF TEST WITH FORMULATION IV (NO TRIS - pH ADJUSTED)

| Room Temp. | | 92% Rel. Humidity | | 56° C. | |
|---|---|---|---|---|---|
| 15 hrs. no differentiation | 33 hrs. no differentiation | 15 hrs. no differentiation | 33 hrs. no differentiation | 15 hrs. reduced differentiation | 48 hrs. no differentiation at lower ketone levels |

Conclusion: Chart V demonstrates that after adjusting the pH of Formulation II, the test strips were essentially of no value. That is, neither the room temperature test strips nor the elevated humidity test strips were able to differentiate among various levels of ketones, the test strips which were subject to an elevated temperature for 15 hours had a reduced ability to resolve the various levels of ketone and the test strips subjected to an elevated temperature for 48 hours were not able to differentiate among the various levels of ketone.

CHART VI
RESULTS OF TEST WITH FORMULATION V (NO TAPS - pH ADJUSTED)

| Room Temp. | | 92% Rel. Humidity | | 56° C. | |
|---|---|---|---|---|---|
| 15 hrs. differentiation | 33 hrs. differentiation | 15 hrs. no differentiation at lower levels | 33 hrs. no differentiation at higher levels erroneous differentiation at lower levels | 15 hrs. poor differentiation | 48 hrs. no differentiation |

Conclusion: The results of Formulation V, demonstrates that, after adjusting the pH of Formulation III the test strips provide satisfactory results only if used promptly. Again there is neither temperature nor humidity stability.

From the above test results we conclude that the combined presence of TAPS and TRIS is critical to providing a system which is stable in response to temperature variations and humidity variations, and which maintains the ability to resolve or differentiate among various levels of ketones.

The foregoing is a complete description of the preferred embodiment of the present invention. It may be appreciated, however, that the composition of the present invention may be embodied in the form of a pressed or molded tablet containing conventional carrier material. To accomplish, this, rather than using water to form the first and second solutions, the ingredients are all in the dry state. Specifically, sodium nitroferricyanide, nickel chloride, TAPS and TRIS are mixed together in the aforementioned proportions and thereafter mixed with a conventional tablet carrier material and thereafter pressed or molded into a plurality of tablets.

What is claimed is:

1. A method for the preparation of a test device for the detection of ketone bodies in body fluids comprising the steps of:
   impregnating a carrier with an aqueous solution of a soluble nitroprusside chromogen;
   drying the impregnated carrier;
   further impregnating the carrier in the area previously impregnated with an aqueous solution including a metal salt, TAPS and TRIS; and
   drying the carrier;
   the pH of the finished test device being no greater than 7.0.

2. The invention as defined in claim 1 wherein said carrier is bibulous.

3. A test device for the detection of ketone bodies in body fluid prepared by the process comprising;
   impregnating a carrier wth an aqueous solution of soluble nitroprusside;
   drying the impregnated carrier;

further impregnating the carrier in the area previously impregnated with an aqueous solution including a metal salt, TAPS and TRIS; and drying the carrier;

the pH of the finished test device being no greater than 7.0.

4. The invention as defined in claim 3 wherein said carrier is bibulous.

5. A test strip for the detection of ketone bodies in body fluids comprising an absorbing material, said absorbing material impregnated with a nitroprusside salt, and thereafter impregnated with a metal salt and the combination of TAPS and TRIS wherein the test strip has a pH no greater than 7.0.

6. A composition for the detection of ketone bodies in body fluids comprising, in combination, a dry mixture of a nitroprusside, a metal salt, TAPS and TRIS, said composition having a pH no greater than 7.0.

* * * * *